(12) United States Patent
Sahni

(10) Patent No.: US 9,408,627 B2
(45) Date of Patent: Aug. 9, 2016

(54) IMAGE GUIDED WHOLE BODY STEREOTACTIC NEEDLE PLACEMENT DEVICE

(76) Inventor: Hirdesh Sahni, Maharashtra (IN)

( * ) Notice: Subject to any disclaimer, the term of this patent is extended or adjusted under 35 U.S.C. 154(b) by 1556 days.

(21) Appl. No.: 12/281,784

(22) PCT Filed: Mar. 6, 2007

(86) PCT No.: PCT/IN2007/000089
§ 371 (c)(1),
(2), (4) Date: Sep. 5, 2008

(87) PCT Pub. No.: WO2008/047379
PCT Pub. Date: Apr. 24, 2008

(65) Prior Publication Data
US 2010/0082040 A1    Apr. 1, 2010

(30) Foreign Application Priority Data
Mar. 7, 2006 (IN) .......................... 319/MUM/2006

(51) Int. Cl.
*A61B 19/00* (2006.01)
*A61B 17/34* (2006.01)

(52) U.S. Cl.
CPC ..... *A61B 17/3403* (2013.01); *A61B 2017/3407* (2013.01)

(58) Field of Classification Search
CPC ................ A61B 19/201; A61B 2019/5236; A61B 2019/524; A61B 2017/3407; A61B 17/3403

USPC .......................................................... 606/130
See application file for complete search history.

(56) References Cited

U.S. PATENT DOCUMENTS

| | | | | |
|---|---|---|---|---|
| 4,608,977 A * | 9/1986 | Brown | ........................... | 606/130 |
| 4,805,615 A * | 2/1989 | Carol | ............................ | 606/130 |
| 4,809,694 A * | 3/1989 | Ferrara | ........................ | 606/130 |
| 5,196,019 A * | 3/1993 | Davis et al. | .................... | 606/130 |
| 5,201,742 A * | 4/1993 | Hasson | ........................ | 606/130 |
| 6,283,977 B1 * | 9/2001 | Ericsson et al. | .............. | 606/130 |
| 6,752,812 B1 * | 6/2004 | Truwit | .......................... | 606/130 |
| 7,636,596 B2 * | 12/2009 | Solar | ............................ | 600/429 |
| 7,824,417 B2 * | 11/2010 | Magnusson et al. | ........... | 606/130 |
| 2004/0167543 A1 * | 8/2004 | Mazzocchi et al. | ............ | 606/130 |
| 2006/0122628 A1 * | 6/2006 | Solar et al. | ..................... | 606/130 |
| 2006/0212044 A1 * | 9/2006 | Bova et al. | ..................... | 606/130 |
| 2009/0148804 A1 * | 6/2009 | Marcus | .............................. | 433/7 |
| 2010/0063516 A1 * | 3/2010 | Parmer et al. | ................. | 606/130 |

* cited by examiner

*Primary Examiner* — Richard Louis

(57) ABSTRACT

The invention provides a an image guided whole body stereotactic needle placement device, for inserting needles or any such medical devices at a desired precise point in a body. The device is used under image guidance obtained from cross sectional imaging by Computerized Tomography and Magnetic Resonance Imaging.
The device has a circular base plate, a semicircular rotating arc that rotates on the base plate, a needle guide that guides the needle placed in a needle sizing tube, a needle guide cover, and a locking pin that locks the needle guide cover to the needle guide.
The device enables immediate detachment of the needle from the device enabling use also in body parts that move with respiration. The device is light weight and small with fixation mechanism to the body such that it can also be used even in newly born.

2 Claims, 9 Drawing Sheets

IMAGE GUIDED WHOLE BODY STEREOTACTIC NEEDLE PLACEMENT DEVICE

FIELD OF INVENTION

This invention relates to an image guided whole body stereotactic needle placement device. More particularly it relates to a computerized tomography (CT) and Magnetic Resonance Imaging (MRI) compatible image guided stereotactic device useful for inserting needles or any such apparatus/medical devices through the said needle at a desired precise point in the body.

In medical field it is very often necessary to precisely position a needle or a medical device through a needle at a particular part of the body or an organ deep inside the body. This is required for obtaining tissue samples for the purpose of diagnosis by histological/biochemical/immunological or any other tests on the obtained samples or for delivering drugs/energy or for therapeutic/palliative aspiration of fluid collections or any such procedure.

This can be done percutaneously under image guidance obtained from cross sectional imaging devices such as ultrasound/CT scan/MRI scan etc. Image guidance is required to select least harmful path for the needle, so as to avoid vital organs and structures such as blood vessels, bowel etc.

These difficult and critical, at times life saving operations/procedures require precise placement of needle/medical devices at precise points or locations in the body while avoiding damage to other delicate organs, tissues, blood vessels etc. Although it is possible to determine exact location using various electronic, sonic or other techniques, guiding the needles to that precise point by free hand is by trial and error and often requires multiple attempts. At times despite multiple attempts it may not be possible to place the needle or such medical device in the desired precise point in the body. At times multiple attempts of passing the needle may cause serious life threatening complications of internal bleeding and/or damage to vital organs in the path of the needle or such device. This can also be better done by using needle guiding devices that can guide the needle in the precise direction so as to reach the precise point in the body in the first attempt.

There are devices available for guiding the needle in a precise direction under ultrasound guidance. There are also devices available for guiding the needle for brain interventions through drilled holes in the skull. However devices available for guiding the needle for brain interventions are not suitable/compatible for use in other parts of the body.

In the modern era of technology various advanced techniques such as CT and MR scanning are available for precise identification of locations needing treatment through placement of needles/medical devices through the needles or for obtaining tissue samples/body fluids. However a universal device capable of using these imaging techniques for precise placement of needles/medical devices through the needles any where in the body is not presently known and hence there is a need to develop such device.

The only reference available in respect of stereo tactic device in medical field is that of a device used for brain surgery/interventions. The said device as described in U.S. patent application Ser. No. 5/26,805 filed on Aug. 26, 2003 and published as publication No. 20060009787A1 on Jan. 12, 2006 the said device comprises a frame, with puncture guides for guiding the tip of a puncturing needle to a predetermined position within the brain, and right and left fixing frames respectively having fixing needles for fixing the device on the patient head, the fixing frames being displaceable in a longitudinal direction of the frame, and the frame being provided with a plurality of guide s for guiding the tip of a puncturing needle toward a point on a line connecting the right and left fixing needles.

The device provided by the abovementioned U.S. patent cannot be used on any other part of the body as it has been designed specifically for brain surgery/interventions only.

None of the existing stereotactic biopsy devices are capable of being used in body part affected by respiratory movement. In order to prevent damage to body organs and tissues in the path of the needle during respiratory movements it is mandatory to allow free movement of the needle or such device during breathing. The present invention provides a stereotactic device that obviates the above limitations. The main object of the present invention is to provide an image guided stereotactic device for needle/medical device placement that could be used for interventions in the entire of the body including brain.

Another object is to provide the said device which is compatible with both CT and MRI scan techniques and environment.

This device can be used in patients of all ages including infants and can be used for whole body including brain and also parts of the body that move with respiration In particular aspect of the present invention the device comprises a base plate at the bottom of the device with a ridge which allows rotation of a needle holder carrying arc, a needle guide with cover for holding the needle sizing tube and a pin to hold together the needle guide, needle guide cover and needle sizing tube.

DETAILED DESCRIPTION OF THE DRAWINGS

Figure 1:
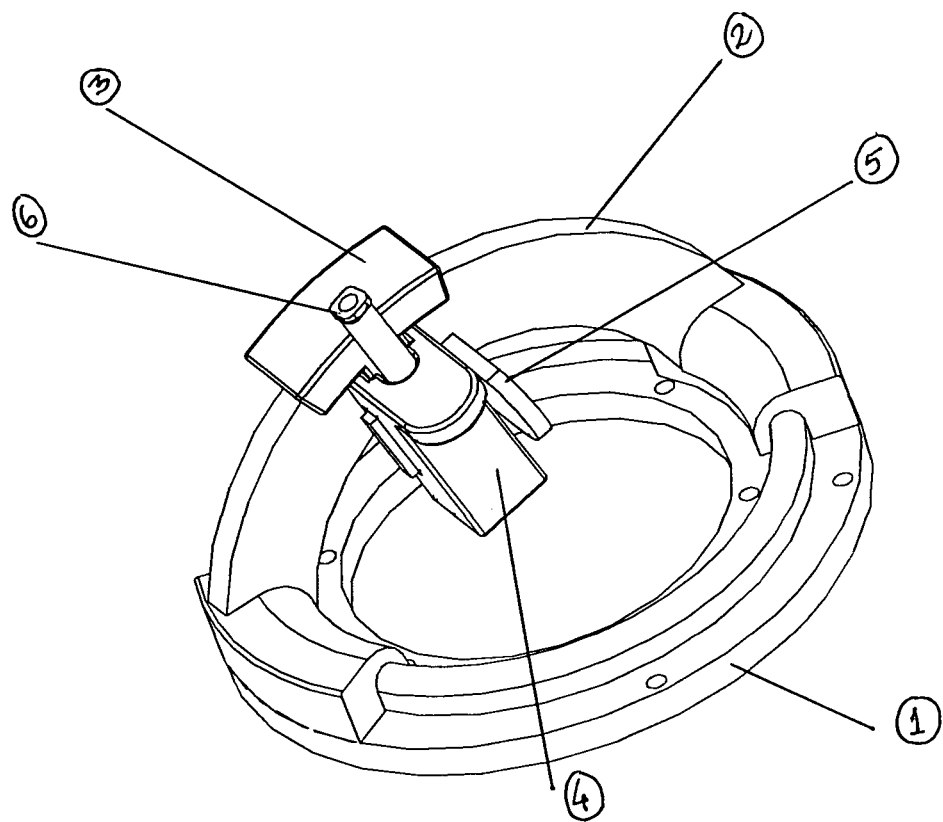
FIG. 1 illustrates a proportional three dimensional view of the device illustrating the main components in working position.
Figure 2:
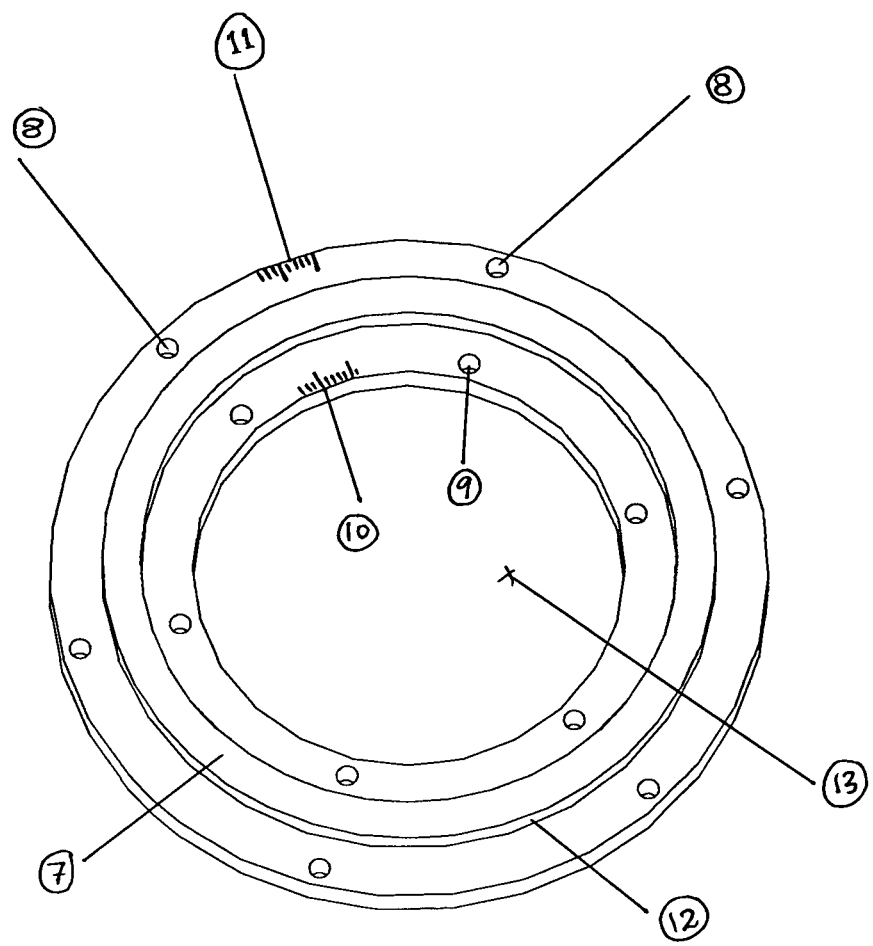
FIG. 2 shows an angled three dimensional top view of the base plate.
Figure 3:
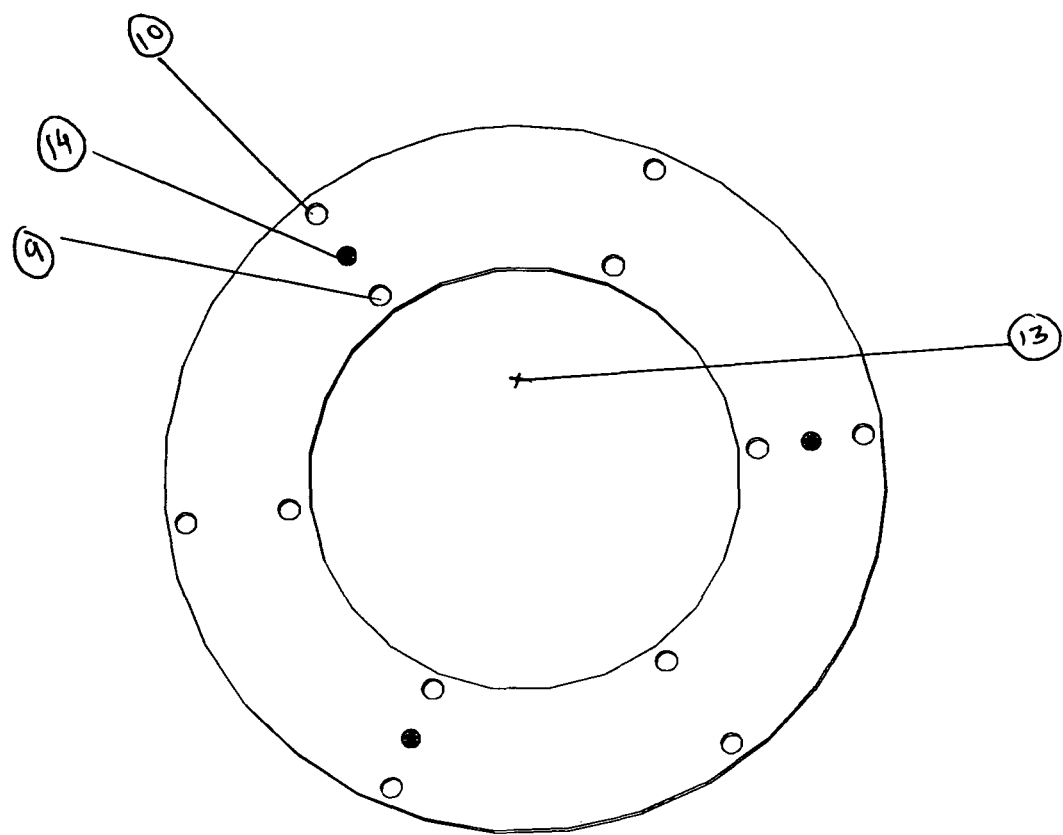
FIG. 3 shows the bottom view of the base plate.
Figure 4:
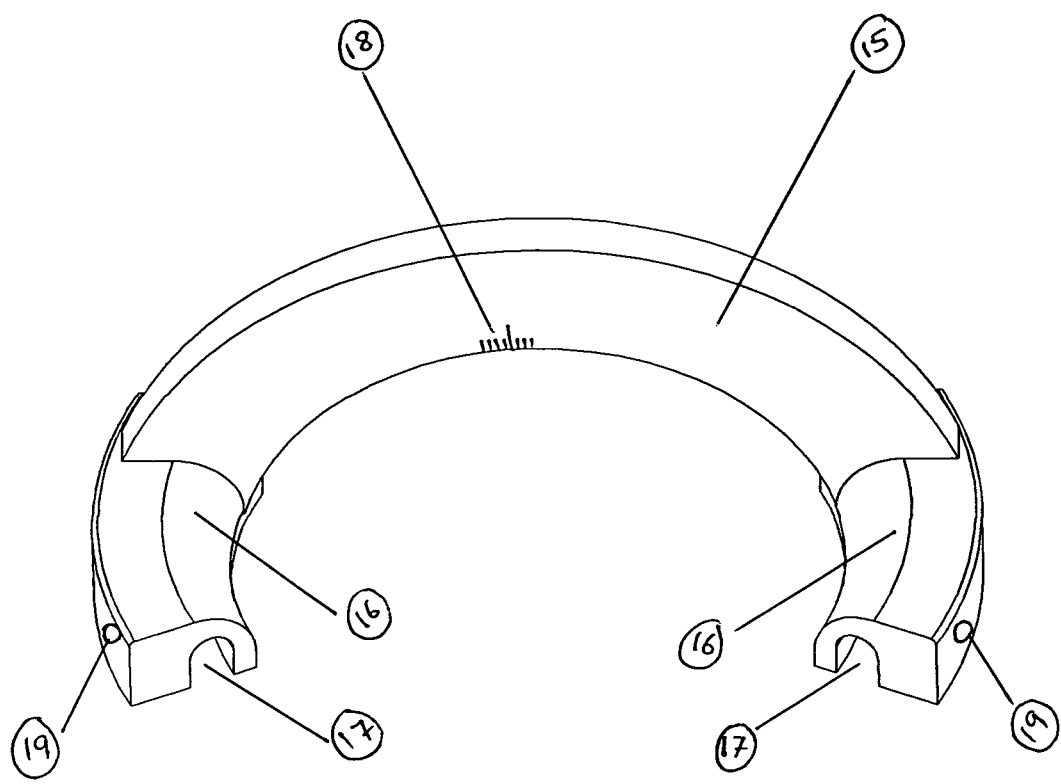
FIG. 4 shows the angled three dimensional front view of the arc.
Figure 5:
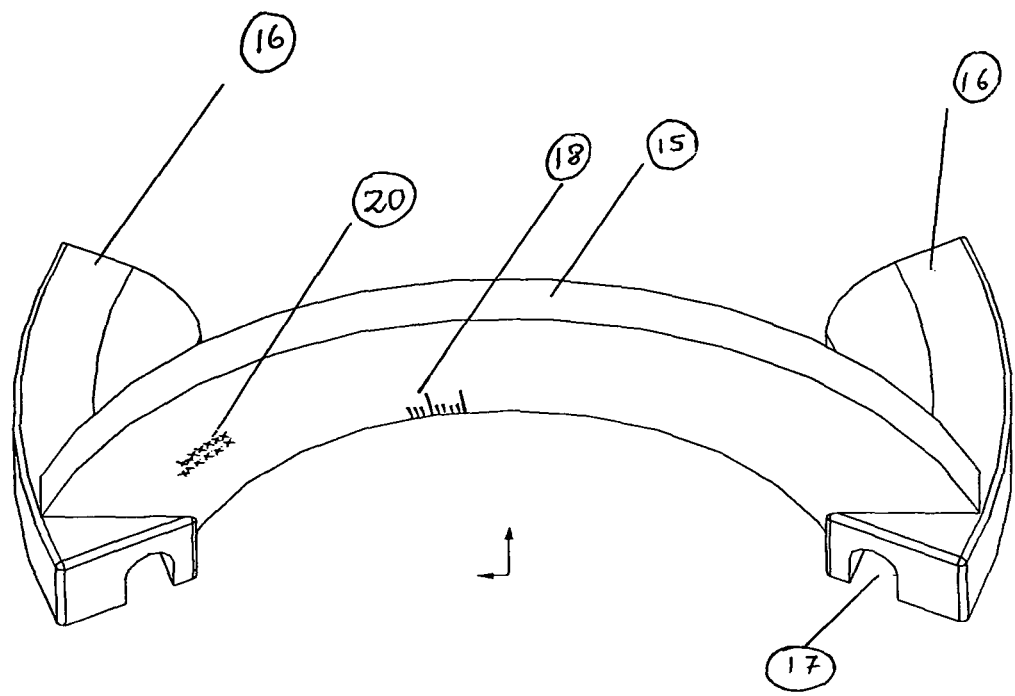
FIG. 5 shows the angled three dimensional back view of the arc.
Figure 6:
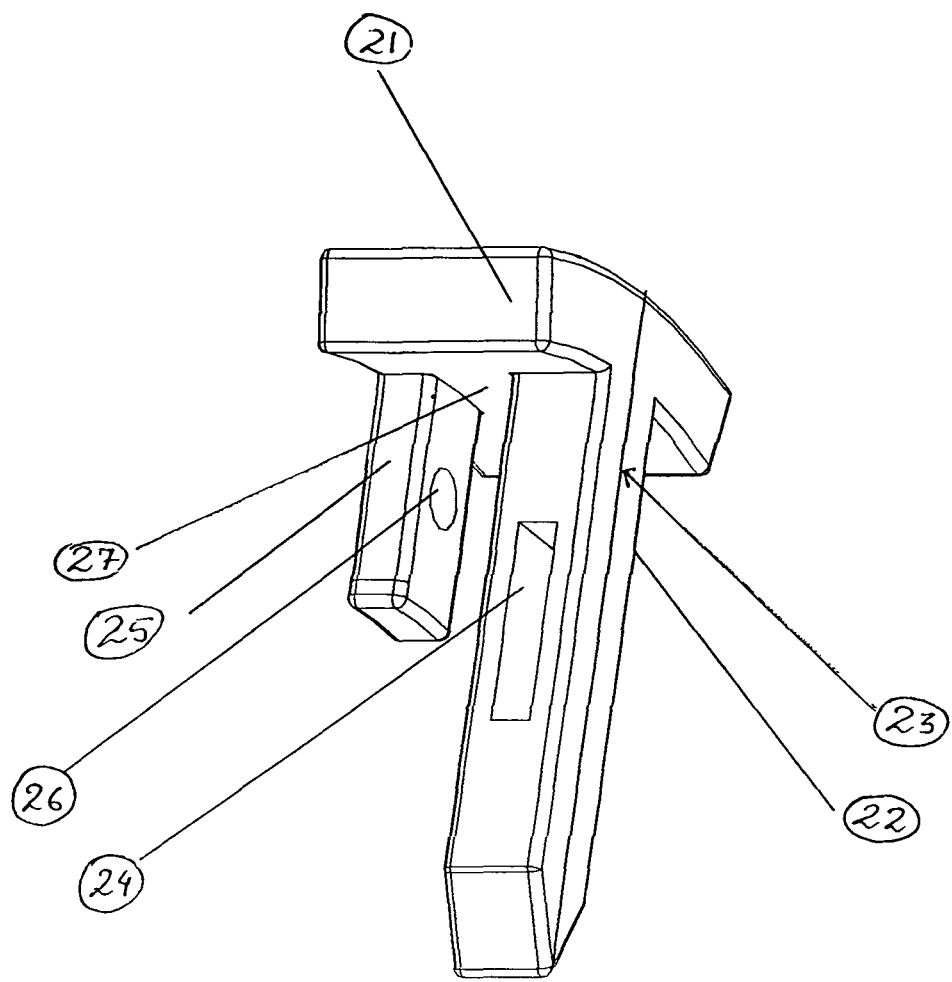
FIG. 6 shows the angled three dimensional side view of the needle guide.
Figure 7:
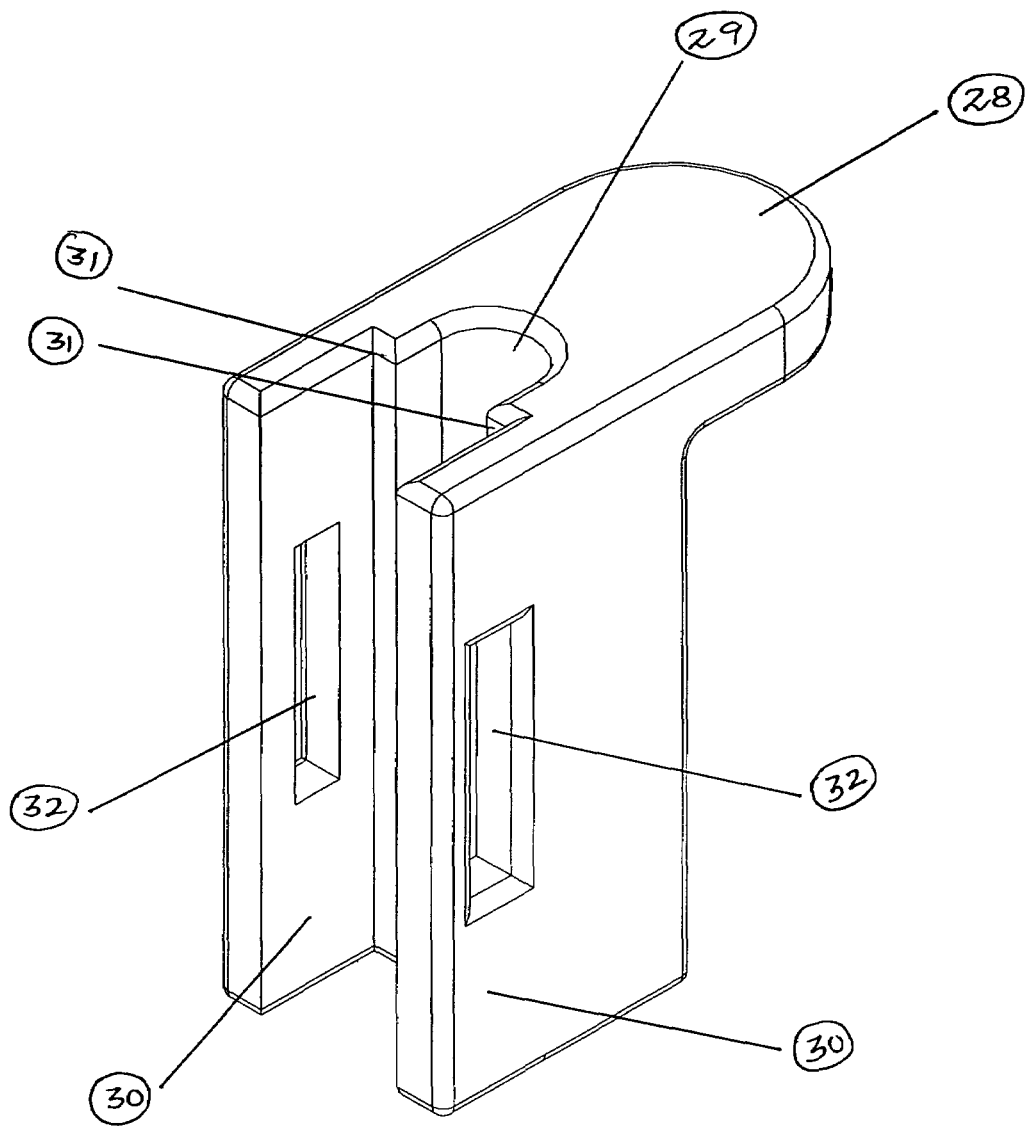
FIG. 7 shows the angled three dimensional bottom view of the needle guide cover.
Figure 8:
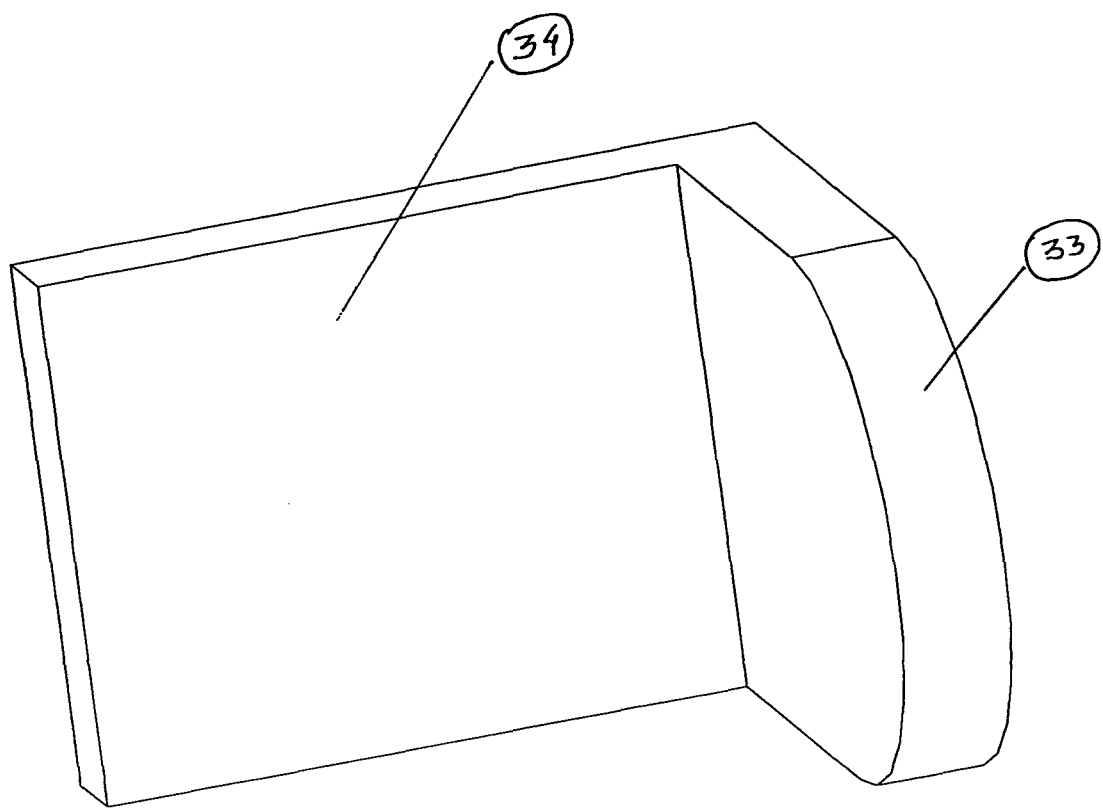
FIG. 8 shows the angled three dimensional front view of the locking pin.
Figure 9:
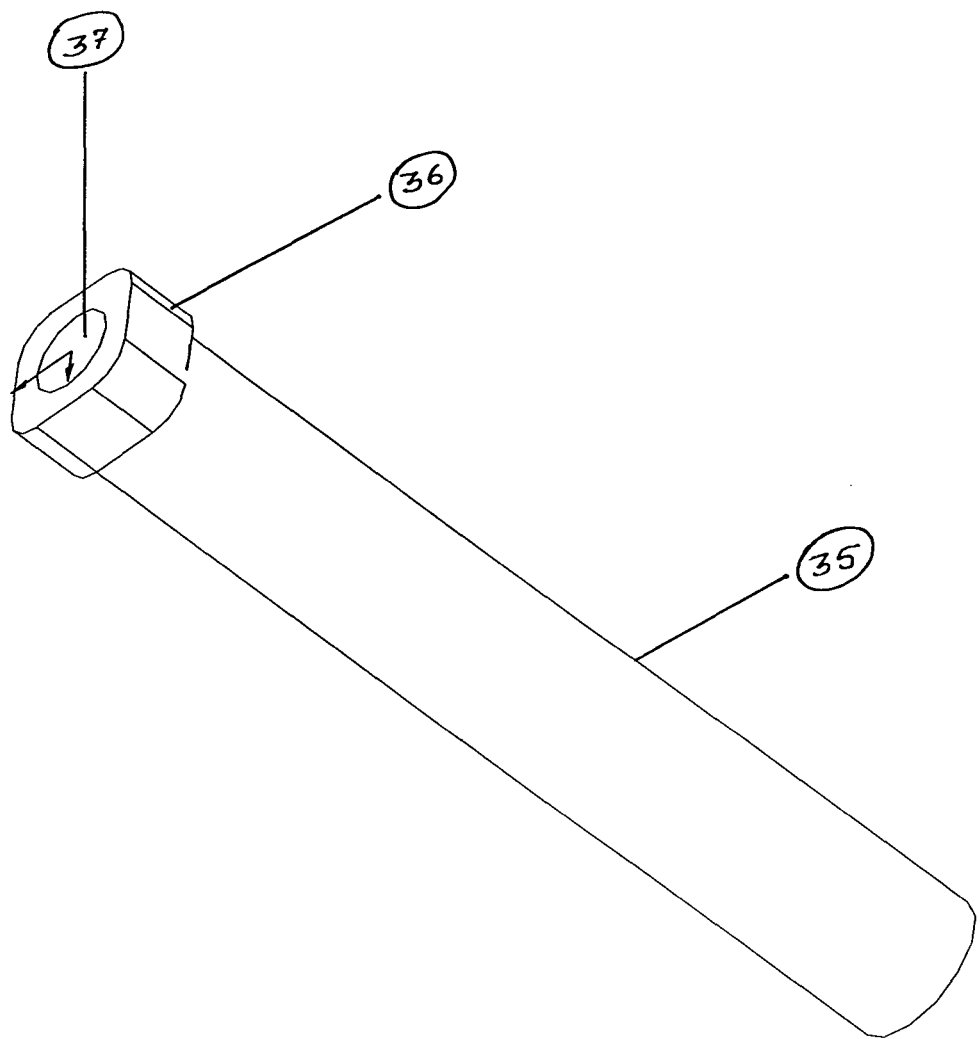
FIG. 9 shows the three dimensional side view of the needle sizing tube.

Referring more particularly to the drawings, FIG.(1) to FIG. (3) illustrate various components of image guided whole body stereotactic needle placement device the device of the present invention in three dimensional perspectives, the device comprising i) a circular base plate (1), having circular ring like base consisting of plane surface at the bottom, with a circular working space (13) and a ridge (7) on the upper surface of the said base having roughened lateral surfaces (12) & outer row (8) of taps for screws/sutures/clips, an inner row (9) of taps for screws/sutures and the inner and outer representative radial markings (10) and (11) for 360 degrees, the bottom surface of the base plate having fiducial markers (14) useful for localizing the base plate (1) in the co-ordinates system of the cross sectional imaging device, such as Computerised Tomography/ Magnetic Resonance Imaging.
  ii) a semicircular arc rotating on the said circular plate (1), the said arc adaptably secured on the ridge (7) of circular plate, a needle guide (3) adaptably secured on the said semicircular arc (2), the said needle guide carrying needle sizing tube (6) covered by the needle guide cover (4).
  iii) The needle sizing tube (6) adaptably secured into the tubular space between the needle guide (3) and the needle cover (4), and all these three held together by the locking pin (5).

Referring to FIG. (4) showing the angled three dimensional front view of semicircular arc (2), comprising the semicircular arc blade (15), the said arc blade resting on foot plates (16) on the both sides of the arc blade (15), the said foot plates being adaptably secured over and capable of rotating over the ridge (7) on the base plate, through grooves (17) in the foot plates (16), the said ridge (7) running the entire circumference of the base plate, and the said groove (17) adaptably fitting over the top of the ridge (7), the foot plate (16) having taps for screw (19) to fix the foot plate (16) to the ridge on base plate (7).

Referring to FIG. (5) describing the three dimensional back view of the arc (2), the arc blade (15) has the roughened track (20) used for securing the screw used to fix the needle guide (3) on the arc blade (15) and also having representative radial markings (18) in degrees all along the arc blade (15).

Referring to FIG.(6) showing the angled three dimensional side view of the needle guide (3) comprising a head (21) for holding the front arm (22) and the back arm (25) separated by a slot bound by contact surface (27) adaptably fitting on the upper side of the arc blade (15). The said front arm (22) protruding from the under surface of the head (21) of the needle guide (3) and the back arm (25) having taps for screw (26) protruding from the back side of the head (21), the said front arm (22) having a tapering at the other end and having a needle track indicator (23) running from the head (21) to the other end of the front arm and a slot (24) for adaptably fitting to the locking pin (5).

Referring to FIG. (7) is the angled three dimensional bottom view of the needle guide cover (4), comprising a grip (28) protruding out of the top of the needle guide cover (4), two parallel restraining walls (30) emanating from the sides of the needle guide cover (4), the said restraining walls (30) having stoppers (31) for front arm (22) of the needle guide (4) in which the said front arms (22) adaptably fitting within the inner restraining walls (30).

The said needle guide cover (4) also providing for a tunnel (29) for needle sizing tube (6) for adaptably holding the said needle sizing tube (6) in the said tunnel (29) and also having slots (32) for locking pin (5).

Referring to FIG. (8) showing the design of the locking pin (5) which comprises a locking plate (34) and grip (33) connected to each other at right angle, the said locking pin adaptably fitting in the slot for locking pin (24) in the front arm (22) of needle guide (3) and the slot for the locking pin (32) of the needle guide cover (4) to hold together the needle guide (3), needle sizing tube (6) and the needle guide cover (4).

Referring to FIG. (9) showing the three dimensional side view of the needle sizing tube (6) which comprises a stem (35) having a collar (36) of slightly larger diameter than the stem (35) and the tunnel for the sizing tube (29) in the needle guide cover (4) so that the collar (36) is always outside the said tunnel (29), having a channel for the needle (37), through which the needle of appropriate size is placed in the needle sizing tube (6), the diameters of channels for needle (37) depending on the diameter of needle/medical device that needs to be positioned into the body.

In one of the features of the present invention the material of making various components has no limitations and these could be made of any suitable material such as metal, polymer etc used in the art, provided it is CT and/or MR Compatible.

In another feature the device of the present invention is fully Computerised Tomography and Magnetic Resonance Imaging compatible.

In yet another feature the image guided whole body stereotactic needle placement device of the present invention could be used in parts of the body that move with respiration as by virtue of its detachable components that can free the needle rapidly.

In still another feature the image guided whole body stereotactic needle placement device could be used in all age groups of patients because of its small size and light weight.

In yet another feature the image guided whole body stereotactic needle placement device could be used in animals, plants, and human beings.

In another feature the image guided whole body stereotactic needle placement device could be used in industrial applications requiring precise placement of needle/device through the needle.

The whole body stereotactic needle placement device provided by the present invention may be used for any part of the human/animal body from where the sample is to be taken for diagnosis or drugs/energy are to be delivered or fluids are to be aspirated for treatment. The CT or MRI scan provide the exact location in the body where the tip of needle/medical device has to be positioned.

The CT/MRI scan of the desired part of the patient's body is performed. The desired point at which the tip of needle/ medical device has to be placed, the desired point of the entry and safest pathway of the needle/medical device is determined from the obtained scans. The base plate (1) is placed on the patient's body, so as to get the desired position of the entry of the needle/medical device in the centre of the working space (13). The base plate is secured to the patient's body by sutures/screws/adhesive tapes if so desired. The CT/MRI scan of the desired part of the patient's body is performed once again. The x, y, z coordinates of the fiducial markers (14) and the desired position of the needle tip/medical device in the patient's body are obtained from the software provided in the CT/MRI scanner. These co-ordinates are fed into suitable computer software, which gives the exact angles of placement of the arc (2) on the base plate (1) and of the needle guide (3) on the arc blade (15). The software also gives the distance to which the needle is to be advanced in the body. These can also be obtained by fixing these co-ordinates on a cuboidal frame specifically designed for this purpose.

Based on the angles obtained by the use of software or the cuboidal frame the needle guide (3) is placed on the arc blade (15) and fixed at the precise degree markings (18) on the arc (2) and the arc foot plates (16) are placed on precise radial markings (10) and (11) on the base plate (1). Once the position of the arc (2) and the needle guide (3) is adjusted these can be secured by placing screws in the tap for screw in footplate (19) and tap for screw in needle guide (26). The needle guide cover (4) is fitted on to the needle guide (3) and secured with locking pin (5) placed through the slots in the needle guide cover (32) and the slots in the needle guide (24).

A small incision appropriate to the diameter of the needle/ medical device to be placed in the patient's body is made at the desired point of entry in the skin. The linear distance between the site of skin entry and the desired position of the needle tip/medical device in the patient's body has been obtained by feeding the co-ordinates of the fiducial markers (14) and the desired position of the needle tip/medical device in the patient's body in a software program/cuboidal frame.

The needle sizing tube (6) with channel (37) of diameter appropriate to the diameter of the needle/medical device proposed to be used is placed into the tunnel for needle sizing tube (29) in the needle guide cover (4). The needle/medical device is advanced to the desired depth.

In case the part of the body where this device is used moves with breathing, it is ensured that the patient is holding breath during passage of needle/medical device. The needle sizing tube is made free by removing the locking pin (5), needle guide cover (4), needle guide (3) and the arc (2) before allowing the patient to breath again.

Once the needle/medical device tip has been positioned at the desired location in the patient's body it can be used to take samples, deliver the drugs/energy or aspirate fluids or to perform any such procedure.

In cases where the placement of needle tip/medical device is not very precise, as determined by the medical practitioner using this device, the needle/medical device could be passed in the body by aligning it to the needle track indicator (23) on the front arm (22) of the needle guide (3). This will not require the use of needle guide cover (4), locking pin (5) and the needle sizing tube (6). This will allow quicker performance of the procedure.

The image guided whole body stereotactic needle placement device provided by the present invention has following advantages:
1. It is CT and MR compatible
2. It enables precise placement of needle in any desired location in the body including brain, thorax, abdomen, extremities etc.
3. It allows use of varying diameter sizes of needles/medical devices.
4. Positioning of the needle could also be done in directions other than the axial plane of the body.
5. The device virtually eliminates multiple attempts to place the needle in desired location along the desired path.
6. It minimizes the morbidity and mortality of the procedure.
7. It increases the success rate of the procedure being performed.
8. It allows use in patients of all ages including infants.

I claim:

1. An image guided whole body stereotactic needle placement device, used to place a needle or a surgical instrument at a desired location in the body and the device consisting of: a circular base plate having a circular ring like base with a circular ridge on the upper surface; a semicircular arc having an arc blade and a foot plate one on each side of the arc blade, the foot plates having a groove on the under surface adapted to accommodate the circular ridge of the circular base plate and the semicircular arc being capable of adaptably rotating over the ridge on the upper surface of circular base plate; a needle guide having a head, a front arm and a back arm, the front arm having a tapered free end and a needle track indicator running from the head to the free end of the front arm, the needle guide being adapted to slide on the arc blade of the semicircular arc with the front arm being on the front of the arc blade and the back arm being on the back of the arc blade and the head touching the arc blade.

2. An image guided whole body stereotactic needle placement device, used to place a needle or a surgical instrument at a desired location in the body and the device consisting of:
a circular base plate having a circular ring like base with a circular ridge on the upper surface;
a semicircular arc having an arc blade and a foot plate one on each side of the arc blade, the foot plates having a groove on the under surface adapted to accommodate the circular ridge of the circular base plate and the semicircular arc being capable of adaptably rotating over the ridge on the upper surface of circular base plate;
a needle guide having a head, a front arm and a back arm, the front arm having a tapered free end, a needle track indicator running from the head to the free end of the front arm, a slot in the front arm for adaptably fitting a locking pin in this slot, the needle guide being adapted to slide on the arc blade of the semicircular arc with the front arm being on the front of the arc blade and the back arm being on the back of the arc blade and the head touching the arc blade;
a needle guide cover having a tunnel/groove for adaptably holding a needle sizing tube, two parallel restraining walls one on each side of the tunnel/groove, the restraining walls adaptably fitting around the front arm of the needle guide, a slot in each of the parallel restraining walls similar to and coinciding with the slot in the front arm of the needle guide for adaptably fitting the locking pin in these slots;
the needle sizing tube having a stem, a collar of slightly larger diameter than the stem and a channel in the stem, the stem adaptably fitting in the tunnel/groove for the needle sizing tube in the needle guide cover and the diameter of the channel being adaptable to the diameter of needle/medical device that needs to be positioned into the body using this device;
the locking pin, having a locking plate and a grip, the locking plate adaptably fitting in the slots in the restraining walls of the needle guide cover and in the slot in the front arm of needle guide, the locking pin being used to adaptably fix the needle guide cover to the needle guide, and consequently hold the needle sizing tube between the needle guide cover and the needle guide, the removal of the locking pin releasing the needle guide cover from the needle guide and consequently freeing the needle sizing tube from the rest of the device.

* * * * *